（12) United States Patent
Couderc et al.

(10) Patent No.: US 11,629,440 B2
(45) Date of Patent: Apr. 18, 2023

(54) METHOD FOR FORMING A BASE KNIT SUITABLE FOR MANUFACTURING HERNIA PROSTHESES AND HERNIA PROSTHESES OBTAINED THEREFROM

(71) Applicant: Sofradim Production, Trevoux (FR)

(72) Inventors: Xavier Couderc, Frans (FR); Jeremy Miralles, Lucenay (FR); Camille Noorman, Lyons (FR)

(73) Assignee: SOFRADIM PRODUCTION, Trevoux (FR)

( * ) Notice: Subject to any disclaimer, the term of this patent is extended or adjusted under 35 U.S.C. 154(b) by 0 days.

(21) Appl. No.: 17/306,463

(22) Filed: May 3, 2021

(65) Prior Publication Data

US 2021/0254247 A1    Aug. 19, 2021

Related U.S. Application Data

(62) Division of application No. 15/965,842, filed on Apr. 28, 2018, now Pat. No. 11,028,509.

(51) Int. Cl.
| | |
|---|---|
| *D04B 21/12* | (2006.01) |
| *D04B 21/16* | (2006.01) |
| *A61F 2/00* | (2006.01) |
| *D04B 27/24* | (2006.01) |

(52) U.S. Cl.
CPC .......... *D04B 21/12* (2013.01); *A61F 2/0063* (2013.01); *D04B 21/16* (2013.01); *D04B 27/24* (2013.01); *A61F 2002/0068* (2013.01); *A61F 2230/0039* (2013.01); *A61F 2240/001* (2013.01); *D10B 2321/022* (2013.01); *D10B 2509/08* (2013.01)

(58) Field of Classification Search
CPC ........ D04B 21/12; D04B 21/06; D04B 21/08; D04B 21/10; D04B 21/24; D04B 21/16; A61F 2/0063; A61F 2/0068
See application file for complete search history.

(56) References Cited

U.S. PATENT DOCUMENTS

| | | | |
|---|---|---|---|
| 4,769,038 A | 9/1988 | Bendavid et al. | |
| 5,141,515 A | 8/1992 | Eberbach | |
| 5,147,374 A | 9/1992 | Fernandez | |
| 5,254,133 A | 10/1993 | Seid | |
| 5,368,602 A | 11/1994 | Torre | |

(Continued)

FOREIGN PATENT DOCUMENTS

| | | |
|---|---|---|
| DE | 69425523 | 6/2001 |
| EP | 3069661 A1 | 9/2016 |

OTHER PUBLICATIONS

Notification of the Third Office Action issued in Chinese application No. 201810385352.1 dated Nov. 3, 2021, with English translation, 8 pages.

(Continued)

*Primary Examiner* — Danny Worrell
(74) *Attorney, Agent, or Firm* — Weber Rosselli & Cannon LLP

(57) ABSTRACT

The invention relates to a method for forming a prosthetic base knit (1) made of two parallel sheets of porous knits, namely a first sheet (2) of porous knit and a second sheet of porous knit, said two parallel sheets being joined together in a discrete manner by a plurality of connecting porous knits (4) spaced apart from each other. The invention further relates to a method for manufacturing H-shaped prostheses for hernia repair from said base knit thus obtained and to the prostheses obtained therefrom.

21 Claims, 4 Drawing Sheets

(56) References Cited

U.S. PATENT DOCUMENTS

| | | | |
|---|---|---|---|
| 5,697,978 | A | 12/1997 | Sgro |
| 5,725,577 | A | 3/1998 | Saxon |
| 6,113,623 | A | 9/2000 | Sgro |
| 6,241,768 | B1 | 6/2001 | Agarwal et al. |
| 6,383,201 | B1 | 5/2002 | Dong |
| 6,451,032 | B1 | 9/2002 | Ory et al. |
| 6,565,580 | B1 | 5/2003 | Beretta |
| 6,596,002 | B2 | 7/2003 | Therin et al. |
| 7,021,086 | B2 | 4/2006 | Ory et al. |
| 9,119,698 | B2 | 9/2015 | Bellon Caneiro et al. |
| 10,472,750 | B2 | 11/2019 | Lecuivre et al. |
| 2004/0054376 | A1 | 3/2004 | Ory et al. |
| 2005/0021058 | A1 | 1/2005 | Negro |
| 2009/0036907 | A1 | 2/2009 | Bayon et al. |
| 2011/0144667 | A1 | 6/2011 | Horton et al. |
| 2012/0082712 | A1 | 4/2012 | Stopek et al. |
| 2012/0179175 | A1 | 7/2012 | Hammell et al. |
| 2013/0345728 | A1 | 12/2013 | Lecuivre et al. |
| 2017/0135797 | A1 | 5/2017 | Lecuivre |

OTHER PUBLICATIONS

Communication pursuant to Article 94(3) EPC issued in European Application No. 17305488.3 dated May 18, 2021, 9 pages.
European Search Report for EP 17305488.3 date of completion is Sep. 6, 2017 (3 pages).
Notification of the First Office Action issued in Chinese application No. 201810385352.1 dated Oct. 10, 2020, with English translation, 25 pages.

METHOD FOR FORMING A BASE KNIT SUITABLE FOR MANUFACTURING HERNIA PROSTHESES AND HERNIA PROSTHESES OBTAINED THEREFROM

CROSS-REFERENCE TO RELATED APPLICATIONS

This application is a divisional application of U.S. patent application Ser. No. 15/965,842 filed on Apr. 28, 2018, which claims the benefit of and priority to European Patent Application Number 17305488.3 filed on May 2, 2017, the disclosure of each of the above-identified applications is hereby incorporated by reference in its entirety.

BACKGROUND

The present invention relates to a method for forming in one single step a prosthetic base knit from which a plurality of H-shaped hernia prostheses may be obtained by a simple cutting step of said base knit. The invention further relates to a method for manufacturing one or more prostheses from said base knit. The invention also relates to a method for forming in one single step a H-shaped prosthesis. The invention further relates to a H-shaped prosthesis formed as a unitary structure having two layers connected by a connector, the dimensions of each layer being independent of the dimensions of the connector.

SUMMARY

The method of the invention allows producing a plurality of H-shaped hernia prosthesis in a reduced time and in a very cost-effective way. The method of the invention further allows manufacturing one piece H-shaped hernia prostheses.

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias or incisional hernias (a hernia occurring through a parietal surgical scar) show themselves in the form of a bulge at the surface of the skin and are classed, for example, as umbilical or inguinal hernias or incisional hernias, depending on where they are located.

A hernia defect may therefore be described as a hole in tissues which are located between the abdominal cavity and the abdominal wall. In order to repair a hernia defect, surgeons often fit a prosthesis in place which is made of one or more sheets of porous synthetic material and replaces or strengthens the weakened anatomical tissues.

In the present application, "porous" is understood as meaning that the material has openings or pores at its surface and within its body. A porous material or porous knit promotes cell recolonization and cellular growth once the prosthesis has been implanted.

In the field of prevention or repair of inguinal hernias, prostheses exist which comprise two sheets of porous material connected together by a connecting section, namely a first sheet of porous material intended to face the abdominal cavity, referred to in the present application as the underlay layer, a second sheet of porous material intended to face the abdominal wall, referred to in the present application as the onlay layer, and a connecting section, connecting the first sheet to the second sheet, and referred to in the present application as the connector. As a result of the intended use of such a prosthesis, said first and second sheets of porous material are more or less located in two parallel planes, and are linked to each other by the connecting section. A transverse cross section of such a prosthesis, i.e transversal to the two parallel planes, forms substantially a H shape, where the underlay layer and the onlay layer form the vertical bars of the H, the connector forming the horizontal bar of the H.

Sheets of porous material for forming hernia prosthesis are advantageously provided as a knitted structure obtained with biocompatible yarns. Knitting methods allow obtaining knitted structure having porous faces that promote cell recolonization after implantation. In addition, knitted structures are sufficiently flexible to be folded up at the time of introduction into the abdominal cavity.

In the existing H-shaped prostheses, the underlay layer, the onlay layer and the connector are generally produced separately and subsequently joined to one another to obtain said H shape. Thus, the method of producing these existing prostheses may be fastidious, long and complicated. The underlay layer, the onlay layer and the connector may be joined, for example, by sewing or else by a thermal welding means. The existing methods for forming H-shaped prostheses are thus time consuming and require a significant number of operations.

There is therefore a need for a method allowing simple and rapid production of a prosthesis that would comprise a structure the transverse cross section of which would substantially form a H, hereinafter referred to for simplicity as a H-shaped prosthesis. In particular, there is a need for a method allowing simple and rapid production of a plurality of such H-shaped prostheses.

In addition, particularly when the underlay layer, the onlay layer and the connector are made of porous material, the joining means, such as sewing or thermal welding means, may create a weakness of the prosthesis, for example a point of weakness at the location where the underlay layer, the onlay layer and the connector are joined together. Once implanted, the prosthesis is subjected to various pressures and/or tensions, for example by the viscera of the abdominal cavity or by the muscles of the abdominal wall, which pressures and/or tensions are generated by the movements and/or efforts made by the patient in his or her daily routine. These points of weakness may therefore prove dangerous for the patient in the event of tearing.

Moreover, solutions for joining together the underlay layer, the onlay layer and the connector in the existing prostheses, either for example by adding a foreign material to the prosthesis or by modifying the chemical structure of the prosthesis by a thermal or mechanical process, are likely to create a discontinuity in the performance of the prosthesis as a whole, and such discontinuity is undesirable.

In addition, the existing methods for joining the connector to the underlay layer and the onlay layer usually confer a rigidity to the liaison between the underlay layer and the connector on one hand, and to the liaison between the connector and the onlay layer on the other hand.

Once an H-shaped prosthesis is in the implantation site and the connector is located in the hernial defect, it may happen that the surgeon need to orientate the underlay layer in an direction slightly different than that conferred by the initial liaison between the connector and the underlay layer. In such a case, the surgeon needs to twist the underlay layer with respect to the connector. The same situation may happen at the liaison between the connector and the onlay layer. In the existing prostheses, such twisting is rendered very difficult and unreliable because of the rigidity between the liaisons between the underlay layer and the connector on one hand, and between the connector and the onlay layer on the other hand.

There is therefore also a need for a H-shaped prosthesis having a good mobility between the underlay layer and the onlay layer, in particular allowing the surgeon to orientate freely the underlay layer on one hand, and the onlay layer on the other hand, regardless from the respective initial orientations of such layers with respect to the connector, and without being impeded in his wish by the potential rigidity of the connector. In particular, the surgeon should be able to twist easily the underlay layer, the onlay layer and the connector one with respect to the other(s). There is also a need for a H-shaped prosthesis with no area of weakness at the joint between the underlay layer, the onlay layer and the connector. In particular, there is a need for a H-shaped prosthesis made as a single unitary structure.

The present invention aims to meet the above needs by providing a method for producing a prosthetic base knit obtainable in a single knitting step, said prosthetic base knit being made of two parallel sheets of porous knits, said two parallel sheets being joined together in a discrete manner by a plurality of connecting knits spaced apart from each other. The present invention further provides a method for manufacturing H-shaped prostheses from such a base knit. The connecting knits being intended to form connectors of H-shaped prostheses, each of the two parallel sheets of the base knit thus obtained may be cut according to a determined shape around each connecting knit, in order to manufacture a H-shaped prosthesis, with the connecting knit forming the connector, one cut sheet of porous knit forming the underlay layer, the other cut sheet of porous knit forming the onlay layer of said prosthesis.

A first aspect of the invention is a method for forming a prosthetic base knit made of two parallel sheets of porous knits, namely a first sheet of porous knit and a second sheet of porous knit, said two parallel sheets being joined together in a discrete manner by a plurality of connecting porous knits spaced apart from each other, said method comprising knitting on a warp knitting machine comprising two needle-beds, a first needle-bed comprising a first guide bar B1, a second guide bar B2 and a third guide bar B3, and a second needle-bed comprising a fourth guide bar B4, a fifth guide bar B5 and a sixth guide bar B6, yarns of a biocompatible material threaded in said first, second, third, fifth and sixth guide bars, according to a defined pattern unit recurring as desired along a warp direction of the machine, said pattern unit corresponding to a total number of N courses ranging from 1 to N completed along said warp direction on each needle-bed, and according to a defined threading-in unit repeated along the width of the knitting machine, said threading-in unit corresponding to a total number T of needles along said width of the machine, N and T being each an integer equal or greater than 5, wherein
  i) for needles ranging from 1 to T and courses ranging from 1 to N, the knitting patterns followed by the first and second guide bars (B1, B2) produce on the first needle-bed said first sheet of porous knit under the form of a first bidimensional porous knit, and the knitting patterns followed by the fifth and sixth guide bars (B5, B6) produce on the second needle-bed said second sheet of porous knit under the form of a second bidimensional porous knit, and
  ii) for needles ranging from w to z, where $1 \leq w < z \leq T$ and courses ranging from x to y, where $1 \leq x < y \leq N$, where w, x, y and z are integers, the knitting pattern followed by the third guide bar B3 produces a connecting porous knit joining said first sheet of porous knit to said second sheet of porous knit, under the form of a three-dimensional porous knit, made of yarns threaded in said third guide bar B3 crossing from the first needle-bed to the second needle-bed and vice-versa.

Another aspect of the invention is a method for manufacturing a H-shaped prosthesis suitable for hernia repair, said H-shaped prosthesis comprising an underlay layer, an onlay layer and a connector, said method comprising the following steps:
  isolating an adequate portion of the base knit obtained according to the knitting method above, said portion including one connecting knit,
  cutting the first sheet of porous knit of said portion to the shape and dimension desired for forming said underlay layer,
  cutting the second sheet of porous knit of said portion to the shape and dimension desired for forming said onlay layer,
  said connecting knit forming said connector.

Another aspect of the invention is a method for manufacturing a H-shaped prosthesis suitable for hernia repair, said H-shaped prosthesis comprising an underlay layer, an onlay layer and a connector, said method comprising the following steps:
  A°) producing a prosthetic base knit made of two parallel sheets of porous knits, namely a first sheet of porous knit and a second sheet of porous knit, said two parallel sheets being joined together by a connecting porous knit, said method comprising knitting on a warp knitting machine comprising two needle-beds, a first needle-bed comprising a first guide bar B1, a second guide bar B2 and a third guide bar B3, and a second needle-bed comprising a fourth guide bar B4, a fifth guide bar B5 and a sixth guide bar B6, yarns of a biocompatible material threaded in said first, second, third, fifth and sixth guide bars, according to a defined pattern unit corresponding to a total number of N courses ranging from 1 to N completed along said warp direction on each needle-bed, and according to a defined threading-in unit corresponding to a total number T of needles along said width of the machine, N and T being each an integer equal or greater than 5, wherein
    i) for needles ranging from 1 to T and courses ranging from 1 to N, the knitting patterns followed by the first and second guide bars (B1, B2) produce on the first needle-bed said first sheet of porous knit under the form of a first bidimensional porous knit, and the knitting patterns followed by the fifth and sixth guide bars (B5, B6) produce on the second needle-bed said second sheet of porous knit under the form of a second bidimensional porous knit, and
    ii) for needles ranging from w to z, where $1 \leq w < z \leq T$ and courses ranging from x to y, where $1 \leq x < y \leq N$, where w, x, y and z are integers, the knitting pattern followed by the third guide bar B3 produces a connecting porous knit joining said first sheet of porous knit to said second sheet of porous knit, under the form of a three-dimensional porous knit, made of yarns threaded in said third guide bar B3 crossing from the first needle-bed to the second needle-bed and vice-versa,
  B°) cutting the first sheet of porous knit to the shape and dimension desired for forming said underlay layer,
  C.°) cutting the second sheet of porous knit to the shape and dimension desired for forming said onlay layer, said connecting knit forming said connector.

The method of the invention allows producing a base knit in one single step, rapidly and efficiently, from which a plurality of H-shaped prostheses may be obtained. Indeed, by cutting the first sheet of porous knit and the second sheet of porous knit located in the vicinity of a connecting knit, a H-shaped prosthesis is obtained. Moreover, not only the base knit, but also all the cut H-shaped prostheses obtained therefrom, are obtained as a unitary structure each.

Moreover, the method of the invention allows designing the underlayer and the onlay layer independently from the dimensions of the connector. In particular, each layer is designed by cutting the corresponding sheet of porous knit around the connecting knit, independently from the length and width of said connecting knit in the plane of said corresponding porous sheet. As a result, the length and width of each layer, namely the underlay layer and the onlay layer, in the plane of said layer, are independent of the length and width of the connector in the plane of said layer.

A further aspect of the invention is a H-shaped prosthesis suitable for hernia repair, said H-shaped prosthesis comprising an underlay layer, an onlay layer and a connector, said underlay layer, onlay layer and connector being formed as an unitary knitted structure, wherein the length and width of each layer are independent of the length and width of said connector in the plane of said layer, the length and width of the connector in the plane of one layer being independent of the length and width of said layer in said plane.

In the method of the invention, since the base knit is obtained as a unitary knitted structure, there is no area of weakness between the first bidimensional porous knit and the connecting knit on one hand, and between the second bidimensional porous knit and the connecting knit on the other hand.

As a consequence, for each H-shaped prosthesis of the invention, in particular cut from the base knit produced according to the method of the invention, there is no area of weakness at the liaisons between the underlay layer and the connector on one hand, and between the onlay layer and the connector on the other hand.

In addition, for each H-shaped prosthesis of the invention, in particular cut from the base knit produced according to the method of the invention, the liaisons between the underlay layer and the connector on one hand, and between the onlay layer and the connector on the other hand show a mobility and a flexibility allowing a surgeon to orientate freely the underlay layer and/or the onlay layer in directions that may differ from the initial orientations of such layers with respect to the connector, without jeopardising the efficiency and the integrity of the H-shaped prosthesis. The surgeon is therefore able to adapt the position of each layer, either underlay layer, onlay layer or both, of the prosthesis to the anatomy of the patient being treated.

In addition, the knitting method of the invention allows using different knitting patterns for the onlay layer and for the underlay layer: the performance characteristic of each layer can therefore be tailored to meet the clinical needs and surgeon preference, in a single manufacturing process without the need for additional manufacturing/assembly steps.

The method for forming the base knit of the invention comprises knitting a plurality of biocompatible yarns on a warp knitting machine comprising two needle-beds, a first needle-bed comprising a first guide bar B1, a second guide bar B2 and a third guide bar B3, and a second needle-bed comprising a fourth guide bar B4, a fifth guide bar B5 and a sixth guide bar B6. The yarns of a biocompatible material are threaded in said first, second, third, fifth and sixth guide bars. The fourth guide bar may be threaded with yarns or not.

The base knit of the invention is produced along the warp direction of the machine by means of the six guide bars operating together and repeating a pattern unit defining the evolution of the yarns. The evolution of a yarn from one needle to another is called a course. The pattern unit corresponds to the smallest number of courses whereby the whole yarn evolution can be described. If a pattern unit corresponds to a total number of N courses, the evolution of the yarn at course (N+1) is the same as that of the first course.

The yarns are threaded in elements of the guide bars according to a threading-in unit. The threading-in unit corresponds to the smallest number of needles, along the width of the machine, whereby the threading-in of the yarns in the guide-bar elements can be described. If a threading-in unit corresponds to a total number of T needles, the threading of the yarn at needle (T+1) is the same as that of the first needle.

In the method of the invention, the base knit is produced according to a defined pattern unit corresponding to a total number of N courses ranging from 1 to N completed along said warp direction on each needle-bed, and according to a defined threading-in unit repeated corresponding to a total number T of needles along said width of the machine, N and T being each an integer equal or greater than 5.

In the method of the invention, the base knit is produced as follows:
i) for needles ranging from 1 to T and courses ranging from 1 to N, the knitting patterns followed by the first and second guide bars (B1, B2) produce on the first needle-bed a first bidimensional porous knit, and the knitting patterns followed by the fifth and sixth guide bars (B5, B6) produce on the second needle-bed a second bidimensional porous knit, and
ii) for needles ranging from w to z, where $1 \leq w < z \leq T$ and courses ranging from x to y, where $1 \leq x < s \leq N$, where w, x, y and z are integers, the knitting pattern followed by the third guide bar B3 produces a three-dimensional porous knit, made of yarns threaded in said third guide bar B3 crossing from the first needle-bed to the second needle-bed and vice-versa.

In the method of the invention, N may be an integer having a value equal or greater than 5, preferably equal or greater than 50, preferably equal or greater than 100, more preferably equal or greater than 200, for example ranging from about 250 to about 850. Actually, N may be any integer suitable with the dimension of the base knit intended to be produced. As an example, with current existing warp knitting machines, knits of at least 100 meters long may be produced. For example, the base knit of the method of the invention is obtained by simply repeating the pattern unit of courses 1 to N as many times as possible on the length of 100 meters.

In the method of the invention, T may be an integer having a value equal or greater than 5, preferably equal or greater than 500, preferably equal or greater than 1000, for example ranging from about 1000 to 6000. T may vary in function of the number of needles set up on the warp knitting machine. In current existing warp knitting machines, a number of needles is present along the width of a knit. As an example, 1644 or more needles may be present on the width of a knit.

In the present application, x, y, w, z, r and s designate a number of courses or a number of needles and are therefore integers.

The warp knitting machine used in the method of the invention comprises two needle-beds. Such double needle-bed machines allow producing bidimensional knits and three-dimensional knits.

In the present application by "bidimensional knit" is meant a knit obtained on a warp knitting machine with the use of one needle-bed only, whatever the number of needle-beds present in the machine, and whatever the number of guide bars present in said one needle-bed. For example, a bidimensional knit may be obtained with two guide bars or more, as long as said guide bars all belong to one needle-bed only.

In the present application by "three-dimensional knit" is meant a knit obtained on a warp knitting machine with the use of two needle-beds, with yarns crossing from a needle-bed to the other.

In the present method, on the whole width of the machine and on the whole production length of the base knit, in other words for needles ranging from 1 to T and courses ranging from 1 to N repeated as many times as said pattern unit and threading-in unit are set to be repeated, the first bidimensional porous knit forms a first sheet of porous knit.

Similarly, on the whole width of the machine and on the whole production length of the base knit, the second bidimensional porous knit forms a second sheet of porous knit.

The first needle-bed and the second needle-bed of a warp knitting machine are parallel. As a result, the first and second sheets of porous knits obtained with the knitting method of the invention are parallel. The distance between the two sheets of porous knits may depend on the distance set up in the machine between the two needle-beds. For example, this distance may range from about 1 mm to about 15 mm, and is preferably about 10 mm.

In the method of the invention, the three dimensional porous knits form connecting porous knits joining the first sheet of porous knit to the second sheet of porous knit. The first sheet of porous knit and the second sheet of porous knit are therefore connected to each other when connecting knits are formed, that is to say when the yarns from the third guide bar B3 cross from the first needle-bed to the second needle-bed and vice versa.

The three dimensional knits being produced only for needles ranging from w to z, where $1 \le w < z \le T$ and courses ranging from x to y, where $1 \le x < y \le N$ for each pattern unit and for each threading-in unit, the connecting porous knits are distributed on the whole area of the base knit in a discrete manner.

The connecting knits of the base knit obtained by the method of the invention are aligned on the warp direction and in the width direction of the machine. Lines of connecting knits may thus be repeated along the width of the machine, depending on the number of times the threading-in is repeated along the width of the machine.

A base knit made of two parallel sheets of porous knits, namely a first sheet of porous knit and a second sheet of porous knit, said two parallel sheets being joined together in a discrete manner by a plurality of connecting porous knits spaced apart from each other is therefore obtained.

It is known that warp knitting machines are capable of producing knits at high production rates. In addition, the knits produced may also show a very long dimension along the warp direction, which is the direction of production of the knit.

As seen above, since knits of at least 100 meters long may be produced with current existing warp knitting machines, the method of the invention allows manufacturing a plurality of connecting knits along the length of 100 meters, and as a consequence a plurality of H-shaped prostheses in a very cost effective way, and in particular in only one knitting step.

As will appear from the description below, the method of the invention allows producing H-shaped prostheses in a very simple, easy and rapid process. In particular the method of the invention is a cost effective process as there is no need to use methods for joining together the various parts of a H-shaped prosthesis, such as the underlay layer, the onlay layer and the connector.

Knits of long dimension in the warp direction, such as knits of 100 meters long, may not be used directly after their production. In such a case, they need to be stored before use. Knits of long dimension in the warp direction are generally stored by being rolled up on a cylinder.

As seen above, a connecting knit of the base knit of the invention connects the first sheet of porous knit to the second sheet of porous knit. In the present application, by "height" of the connecting knit, or of the connector, is understood the distance between the first sheet of porous sheet, or underlay layer, and the second porous sheet, or onlay layer, said distance including the respective thickness of said sheet/layer, as shown on FIG. 1. The height of the connecting knit of the base knit of the invention depends on the distance selected between the first needle-bed and the second needle-bed of the warp knitting machine. The height of the connecting knit is determined in function of the desired height of the connector of the H-shaped prostheses that will be manufactured from the base knit of the invention. During storage on a cylinder in a rolled-up status, the weight of the rolled layers of base knit may apply a pressure on the connecting knits present in the base knit. The result may be that, after a certain time of storage, the height of the connecting knits may have varied, and in particular, may have decreased. Such a phenomenon is not desirable and is not compatible with the aim of manufacturing reproducible H-shaped prostheses.

In embodiments, said fourth guide bar B4 being threaded with yarns of a biocompatible material, for needles ranging from r to s, where $1 \le r < s < w < z \le T$ or $1 \le w < z < r < s \le T$, and courses ranging from 1 to N, the knitting pattern of the fourth guide bar B4 produces a pillar knit joining said first sheet of porous knit to said second sheet of porous knit, under the form of a three-dimensional knit made of yarns threaded in said fourth guide bar B4 crossing from the first needle-bed to the second needle-bed and vice-versa.

Such pillar knits run along the warp direction of the base knit so as to maintain a constant distance between the first sheet of porous knit and the second sheet of porous knit on the whole area of the base knit. The pillar knits may run along the warp direction of the base knit either in a continuous way or in a discontinuous way, as long as they maintain a constant distance between the first sheet of porous knit and the second sheet of porous knit. For example, having pillar knits running along the warp direction of the base knit in a discontinuous way allows providing visual markings for identifying the locations of the connecting knits, and therefore locations where the base knit is to be cut further on for isolating an adequate portion intended to produce a H-shaped prosthesis. In particular, the pillar knits are not intended to be used in the manufacture of the H-shaped prostheses obtainable from the base knit. The pillar knits are intended to preserve a correct height of the connecting knits of the base knit, in particular when the base knit is rolled up on a cylinder for storage, so that the connecting knits intended to be used as connectors in the manufacture of the H-shaped prostheses are not squeezed by the weight of the rolled-up base knit.

The bidimensional porous knits forming the first and second sheets of porous knits of the method of the invention are capable of favoring cellular growth and may be obtained thanks to all knitting patterns known from the art allowing to produce a knit with pores, voids, etc. using only one needle bed of a warp knitting machine. Such knitting patterns are well known. The knitting pattern used for the first sheet of porous knit may be the same or different from the knitting pattern used for the second sheet of porous knit.

Examples of knitting two-dimensional knits suitable for the present invention are given in documents WO99/05990, WO2009/031035 and WO2009/071998.

The first sheet of porous knit is intended to form the underlay layer of the H-shaped prosthesis obtainable from the base knit of the invention. The underlay layer is intended to face the abdominal cavity and to repair the hernia defect as such. In this view, it constitutes the part of the prosthesis that will provide the biggest part of the mechanical support necessary to repair the hernia. Moreover, it is desirable that the underlay layer shows certain rigidity so that it can deploy easily in the abdominal cavity after it has been folded on itself in order to be conveyed to the implantation site. In embodiments, the knitting patterns followed by guide-bars B1 and B2 allow producing a first sheet of porous knit showing adequate pore size and mechanical properties so that the underlay layer may both deploy easily in the abdominal cavity and perform efficiently its wall reinforcing function.

In embodiments, the knitting patterns followed by guide-bars B1 and B2 allow producing a first sheet of porous knit having a pore size, measured according to the method described in Example 1 of the present application, as follows:
Pore (width mm×height mm): ranging from about 1.0 mm to about 3.0 mm, preferably of about 1.1 mm×1.7 mm.

Such pore size allows obtaining a first sheet of porous knit showing good mechanical property.

In embodiments, the knitting patterns followed by guide-bars B1 and B2 allow producing a first sheet of porous knit showing a tensile breaking strength, measured according to the method described in Example 1 of the present application, ranging from about 100 N to about 1200 N, preferably from about 300 N to about 1000 N, preferably from about 500 to about 900 N, more preferably of about 625 N, in the warp direction, and ranging from about 100 N to about 1200 N, preferably from about 120 N to about 1000 N, preferably from about 200 N to about 500 N, more preferably of about 278 N in the weft direction. Such tensile breaking strength allows obtaining a first sheet of porous knit showing good mechanical support.

In embodiments, the knitting patterns followed by guide-bars B1 and B2 allow producing a first sheet of porous knit showing a bending rigidity, measured according to the method described in Example 1 of the present application, ranging from about 60 g to about 100 g, preferably of about 72 g. Such a bending rigidity allows obtaining a first sheet of porous knit showing a good capability to deploy itself automatically after having been folded on itself.

In embodiments, the knitting pattern followed by guide bars B 1, B2, is the following, according to the ISO 11676 standard (publication year 2014):
B1: (3-2-2-2/2-1-1-1/0-1-2-2)
B2: (2-3-3-3/3-4-4-4/5-4-3-3)
where guide bars B1 and B2 are threaded one full one empty with monofilaments of polypropylene. The first sheet of porous knit thus obtained shows the following properties:
Pore size (width mm×height mm): 1.1 mm×1.7 mm,
Tensile breaking strength: 625 N in the warp direction and 278 N in the weft direction,
Bending rigidity: 72 g The second sheet of porous knit is intended to form the onlay layer of the H-shaped prosthesis obtainable from the base knit of the invention. The onlay layer is intended to face the abdominal wall, to provide additional support to the underlay layer, to cover the entire floor of the inguinal canal and to secure optimal positioning of the entire prosthesis. In this view, it is desirable that the onlay layer shows a good flexibility, a good transparency and a good conformability so that it can be positioned easily. The onlay layer may also be sutured and should preferably show a good suture pull out strength. In embodiments, the knitting patterns followed by guide-bars B5 and B6 allow producing a second sheet of porous knit showing adequate pore size and physical properties so that the onlay layer may show a good flexibility and a good conformability.

In embodiments, the knitting patterns followed by guide-bars B5 and B6 allow producing a second sheet of porous knit having a pore size, measured according to the method described in Example 1 of the present application, ranging from about 1.7 mm×3.1 mm, preferably from about 1.5 mm to about 1.5 mm. Such pore size allows obtaining a second sheet of porous knit showing a good flexibility and a good conformability.

In embodiments, the knitting patterns followed by guide-bars B5 and B6 allow producing a second sheet of porous knit having a suture pull out strength, measured according to the method described in Example 1 of the present application, ranging from about 20 N to about 80 N, preferably from about 30 N to about 70 N, more preferably of about 43 N in the warp direction, and ranging from about 20 N to about 80 N, preferably from about 30 N to about 70 N, preferably of about 42 N in the weft direction. Such a suture pull out strength allows obtaining a second sheet of porous knit showing a good suturability.

In embodiments, the knitting pattern followed by guide bars B5, B6, is the following, according to the ISO 11676 standard (publication year 2014):
B5: (2-2-1-0/1-1-1-2/1-1-1-0/1-1-1-2/4-4-6-7/6-6-6-5/6-6-6-7/6-6-6-5)
B6: (5-5-6-7/6-6-6-5/6-6-6-7/6-6-6-5/3-3-1-0/1-1-1-2/1-1-0/1-1-1-2)
where guide bars B5 and B6 are threaded one full one empty with monofilaments of polypropylene. The second sheet of porous knit thus obtained shows the following properties:
Pore size: 1.7 mm×3.1 mm
Suture pull out strength: 43 N in the warp direction and 42 N in the weft direction.

The three-dimensional porous knit forming the connecting knits of the method of the invention is capable of favoring cellular growth and may be obtained thanks to all knitting patterns known from the art allowing to produce a knit with pores, voids, etc. . . . on a double needle-bed warp machine by using the two needle-beds of the machine. Such knitting patterns are well known.

The connecting knits of the base knit of the invention are intended to form the connectors of the H-shaped prosthesis obtainable from the base knit of the invention. The connector is intended to connect the underlay layer to the onlay layer and may also to the hernia defect. The connector should therefore be flexible and mechanically resistant. In embodiments, the knitting pattern followed by guide-bar B3 allows producing a connecting knit showing good flexibility and good tensile breaking strength and elongation.

In embodiments, the knitting pattern followed by guide-bar B3 allows producing a connecting knit showing a tensile breaking strength, measured according to the method described in Example 1 of the present application, ranging from about 30 N to 200 N, preferably from about 80 N to about 180 N, preferably from about 110 N to about 160 N, more preferably of about 139 N, in the warp direction and ranging from about 30 N to 200 N, preferably from about 80 N to about 180 N, preferably from about 110 N to about 160 N, preferably of about 143 N in the weft direction.

In embodiments, the knitting pattern followed by guide-bar B3 allows producing a connecting knit showing a tensile elongation under 50N, measured according to the method described in Example 1 of the present application, ranging from about 20% to 100%, preferably of about 36% in the warp direction and ranging from about 20% to 100%, preferably of about 54% in the weft direction.

In embodiments, the knitting pattern followed by guide-bar B3 allows producing a connecting knit showing a tensile elongation at break, measured according to the method described in Example 1 of the present application, ranging from about 60% to about 200%, preferably of about 72% in the warp direction and ranging from about 60% to about 200% preferably of about 112% in the weft direction.

In embodiments, the knitting pattern followed by guide bar B3 is the following, according to the ISO 11676 standard (publication year 2014):

B3: (2-3-3-2/3-4-3-2/5-4-4-5)

where guide bar B3 is threaded one full one empty with monofilaments of polypropylene. The connecting knit thus obtained shows the following properties:

Tensile breaking strength: 139 N in the warp direction and 143 N in the weft direction,
Tensile elongation under 50N: 36% in the warp direction and 54% in the weft direction,
Tensile elongation at break: 72% in the warp direction and 112% in the weft direction.

The three-dimensional knit forming the pillar knits of the method of the invention may be obtained thanks to all knitting patterns allowing the crossing of yarns from the first needle-bed to the second needle-bed.

In embodiments, wherein N is equal to 264, the knitting pattern followed by guide bars B1, B2, B3, B5 and B6 is the following, according to the ISO 11676 standard (publication year 2014):

B1: (3-2-2-2/2-1-1-1/0-1-2-2)×88//
B2: (2-3-3-3/3-4-4-4/5-4-3-3)×88//
B3: (2-3-3-3/3-4-4-4/5-4-3-3)×36/(2-3-3-2/3-4-3-2/5-4-4-5)×3/(2-3-3-3/3-4-4-4/5-4-3-3)×49//
B5: (2-2-1-0/1-1-1-2/1-1-1-0/1-1-1-2/4-4-6-7/6-6-6-5/6-6-6-7/6-6-6-5)×33//
B6: (5-5-6-7/6-6-6-5/6-6-6-7/6-6-6-5/3-3-1-0/1-1-1-2/1-1-1-0/1-1-1-2)×33//

In embodiments where the guide bar B4 is threaded, the knitting pattern followed by B4 may be the following, according to the ISO 11676 standard (publication year 2014):

B4: (2-3-3-2/3-4-3-2/5-4-4-5)×75/1-1-1-2/1-1-1-0/1-1-1-2/4-4-6-7/6-6-6-5/6-6-6-7/6-6-6-5/(2-2-1-0/1-1-1-2/1-1-1-0/1-1-1-2/4-4-6-7/6-6-6-5/6-5-6-7/6-6-6-5)×4//

For example, the values of x, y, w, z, r and s of the method of the invention may the following:
x=109,
y=117,
w=67,
z=74,
r=141,
s=156.

In embodiments, T being equal to 156, the threading-in of bars B1, B2, B3, B4, B5 and B6 is the following:

B1: (D.)78
B2: (S.)2(D.)31(S.)4(D.)31(S.)10
B3: (S.)2.62(S.)4.62(S.)2.16
B4: 0.140(S.)8
B5: (S.)78
B6: (S.)78

Wherein a dot "." means one element empty, "D" means two yarns, "S" means a single yarn, therefore:

(D.) means one element full, one element empty, where the one element full is threaded with two yarns (Double yarn),
(S.) means one element full, one element empty, where the one element full is threaded with one yarn only (Single yarn).

For example, the threading in of bar B2 above means: two times "one element full threaded with one yarn, one element empty", thirty-one times "one element full threaded with two yarns, one element empty", four times "one element full threaded with one yarn, one element empty", thirty-one times "one element full threaded with two yarns, one element empty", ten times "one element full threaded with one yarn, one element empty".

For example, the threading in of bar B3 above means: two times "one element full threaded with one yarn, one element empty", sixty-two elements empty, four times "one element full threaded with one yarn, one element empty", sixty-two elements empty, two times "one element full threaded with one yarn, one element empty", sixteen elements empty.

In other embodiments, wherein N is equal to 216, the knitting pattern followed by guide bars B1, B2, B3, B5 and B6 is the following, according to the ISO 11676 standard (publication year 2014):

B1: (3-2-2-2/2-1-1-1/0-1-2-2//)×72
B2: (2-3-3-3/3-4-4-4/5-4-3-3//)×72
B3: (2-3-3-3/3-4-4-4/5-4-3-3)×65/(2-3-3-2/3-4-3-2/5-4-4-5)×5/2-3-3-2/3-4-4-5/5-4-3-3/2-3-3-3/3-4-4-4/5-4-3-3//
B5: (2-2-1-0/1-1-1-2/1-1-1-0/1-1-1-2/4-4-6-7/6-6-6-5/6-6-7/6-6-6-5//)×27
B6: (5-5-6-7/6-6-6-5/6-6-6-7/6-6-6-5/3-3-1-0/1-1-1-2/1-1-0/1-1-1-2//)×27

If guide bar B4 is threaded, its knitting pattern is the following according to the ISO 11676 standard (publication year 2014):

B4: (2-3-3-2/3-4-3-2/5-4-4-5)×36/3-2-1-0/(1-1-1-2/3-3-4-5/4-4-4-3/2-2-1-0)×4/1-1-1-2/(2-3-3-2/3-4-3-2/5-4-4-5)×30//

And, T being equal to 156, the threading-in is the following:

B1: (D.)78
B2: (D.)31(S.)8(D.)31(S.)8
B3: 0.62(S.)8.78
B4: 0.140(S.)8
B5: (S.)78
B6: (S.)78 wherein the ".", D and S have the same meaning as described above.

In embodiments, the distance between the first needle-bed and the second needle-bed is set at a value ranging from about 1 mm to about 15 mm, preferably is about 10 mm. As a consequence, the height of the connecting knits of the base knit is approximately 10 mm.

The yarns threaded in the guide bars of the warp knitting machine used in the method of the invention may be monofilaments or multifilaments. In embodiments, the yarns are monofilaments. For example, the yarns may be selected from monofilaments having a diameter ranging from about 0.07 mm to about 0.30 mm, for example of about 0.12 mm.

The yarns used for forming the base knit in the method of the invention are made of a biocompatible material. The biocompatible material may be identical or different from one yarn to another. The biocompatible material may be synthetic or natural. The biocompatible material may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The biocompatible material may be selected from the group consisting of biodegradable polymers, non-biodegradable polymers, and combinations thereof.

Non-biodegradable materials that may be used as biocompatible material for the yarns of the method of the invention include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; polytetrafluoroethylene; polyether-esters such as polybutester; polytetramethylene ether glycol; 1,4-butanediol; polyurethanes; and combinations thereof. In other embodiments, non-degradable materials may include silk, collagen, cotton, linen, carbon fibers, titanium, and the like. The polypropylene may be isotactic polypropylene or a mixture of isotactic and syndiotactic or atactic polypropylene.

Biodegradable materials that may be used as biocompatible material of the yarns of the method of the invention include polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these materials and mixtures thereof.

In embodiments, the biocompatible material is selected from polyethylene, polypropylene, polyester such as polyethylene terephthalates, polyamide, silicone, polyether ether ketone (PEEK), polyarylether ether ketone (PAEK), polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the biocompatible material is polypropylene.

In embodiments, all the yarns are polypropylene monofilaments.

In embodiments, the method of the invention further comprises a heat-setting step during which the base knit is submitted to a heat-setting treatment. A heat-setting treatment is usually completed in order to stabilize a knit in width and length, in particular in the weft direction and in the warp direction. The knit is usually kept under no tension, neither in the warp direction nor in the weft direction, during the heat-setting step.

In the present application, the base knit of the invention comprises a first sheet of porous knit and a second sheet of porous knit which may be made from different yarns and which may show different knitting patterns. The heat-setting step should therefore take into account the difference of nature and/or structure between the two sheets of porous knits and be adapted so as to obtain an acceptable stabilization of both sheets.

Moreover, the base knit of the invention further includes connecting knits which comprise yarns crossing from the first sheet of porous knit to the second sheet of porous knit along a direction that is perpendicular to the plane including both the warp direction and to the weft direction of said first and second sheets of porous knits. It has been observed that heating the connecting knit could lead to a certain shrinkage of the height of the connecting knit. It would be desirable to perform a heat-setting step preserving the height of the connecting knit. Indeed, as seen above, the height of the connector of the H-shaped prosthesis obtainable from the base knit of the invention depends on the height of the connecting knit. The height of the connector of the H-shaped prosthesis should be reproducible. Indeed uncontrolled shrinkage of the height of the connector could impact the performance of the H-shaped prosthesis once implanted, by not leaving enough distance between the onlay layer and the underlay layer. As a result, one or both of those layers could be partially pulled into the space of the hernia defect and disrupt the placement and fixation of the prosthesis.

In embodiments, the heat-setting treatment is performed at a temperature allowing both i) an acceptable stabilization of the first and second sheets of porous knits and ii) a shrinkage of the connecting knit's height of less than 80%, preferably less than 75%, more preferably of about 50%.

For example, the heat-setting treatment is performed at a temperature ranging from about 90° C. to about 250° C., preferably from about 110° C. to about 240° C., preferably from about 130° C. to about 145° C., more preferably at about 140° C.

For example, when the base knit is made of polypropylene yarns, the heat-setting treatment may comprise a step of heating the base knit at a temperature ranging from about 130° C. to about 145° C., preferably of about 140° C. The first and second sheets of porous knits are therefore well stabilized in the weft direction and in the warp direction and the height of the connecting knit may show a shrinkage of about 50%.

In embodiments, after the heat-setting treatment, the height of the connecting knits, intended to form the connectors of the H-shaped prostheses, ranges preferably from about 3 mm to about 7 mm, preferably is about 5 mm.

The invention further relates to a method for manufacturing a H-shaped prosthesis suitable for hernia repair from the base knit above, said H-shaped prosthesis comprising an underlay layer, an onlay layer and a connector. The method comprises therefore the following steps:

isolating an adequate portion of the base knit obtained according to the knitting method described above, said portion including one connecting knit, cutting the first sheet of porous knit of said portion to the shape and dimension desired for forming said underlay layer, cutting the second sheet of porous knit of said portion to the shape and dimension desired for forming said onlay layer, said connecting knit forming said connector.

The isolating step may be performed by any method allowing to separate the requested adequate portion from the rest of the base knit obtained: for example, the isolating step may be performed manually by cutting the adequate portion with a pair of scissors, or alternatively automatically by using a punch. The adequate portion may be separated from the rest of the base knit by any cutting means such as a laser, high frequency welding, water jet, heating element, etc. . . .

Alternatively, in embodiments, the base knit may be produced for the manufacture of one H-shaped prosthesis only, in which case the pattern unit and the threading-in unit are followed only once and are not recurring along the production length and the width of the machine. In such embodiments, the method for manufacturing one H-shaped prosthesis suitable for hernia repair, said H-shaped prosthesis comprising an underlay layer, an onlay layer and a connector, comprises the following steps:

A°) producing a prosthetic base knit made of two parallel sheets of porous knits, namely a first sheet of porous knit and a second sheet of porous knit, said two parallel sheets being joined together by a connecting porous knit, said method comprising knitting on a warp knitting machine comprising two needle-beds, a first needle-bed comprising a first guide bar B1, a second guide bar B2 and a third guide bar B3, and a second needle-bed comprising a fourth guide bar B4, a fifth guide bar B5 and a sixth guide bar B6, yarns of a biocompatible material threaded in said first, second, third, fifth and sixth guide bars, according to a defined pattern unit corresponding to a total number of N courses ranging from 1 to N completed along said warp direction on each needle-bed, and according to a defined threading-in unit corresponding to a total number T of needles along said width of the machine, N and T being each an integer equal or greater than 5, wherein
  i) for needles ranging from 1 to T and courses ranging from 1 to N, the knitting patterns followed by the first and second guide bars (B1, B2) produce on the first needle-bed said first sheet of porous knit under the form of a first bidimensional porous knit, and the knitting patterns followed by the fifth and sixth guide bars (B5, B6) produce on the second needle-bed said second sheet of porous knit under the form of a second bidimensional porous knit, and
  ii) for needles ranging from w to z, where $1 \leq w < z \leq T$ and courses ranging from x to y, where $1 \leq x < y \leq N$, where w, x, y and z are integers, the knitting pattern followed by the third guide bar B3 produces a connecting porous knit joining said first sheet of porous knit to said second sheet of porous knit, under the form of a three-dimensional porous knit, made of yarns threaded in said third guide bar B3 crossing from the first needle-bed to the second needle-bed and vice-versa, B°) cutting the first sheet of porous knit to the shape and dimension desired for forming said underlay layer, C.°) cutting the second sheet of porous knit to the shape and dimension desired for forming said onlay layer, said connecting knit forming said connector.

Whatever the size of the base knit of the invention obtained, either by recurring the pattern unit and threading-in unit along the production length and the width of the machine or not, the further cutting of each sheet of porous knit allows designing the underlay layer and the onlay layer as desired. Each of the underlay layer and onlay layer may be cut and designed so as to show a shape suitable for covering the hernia defect in relation with the part of the anatomy where said layer is intended to be located. Said shape may be rectangular, square, circular, oval, etc. For example, the underlay layer may be cut so as to show a circular shape. The onlay layer may be cut so as to show an oval shape.

For example, if the length and width of one layer, either underlay layer or onlay layer, or of the connector, are defined, after cutting, as being respectively the dimension of said layer or connector in the warp direction (length) and the dimension of said layer or connector in the weft direction (width), each layer is designed by cutting the corresponding sheet of porous knit around the connecting knit, independently from the length and width of said connecting knit/connector in the plane of said corresponding porous sheet. As a result, the length and width of each layer, namely the underlay layer and the onlay layer, in the plane of said layer, are independent of the length and width of the connector in the plane of said layer. In the same way, the length and width of the connector in the plane of either layer are independent of the length and width of said layer in said plane.

The H-shaped prostheses obtained by the manufacturing method of the invention show therefore a unitary structure and are free of any weaknesses at the liaisons between the onlay layer and the connector on one hand, and between the underlay layer and the connector on the other hand.

In addition, thanks to the structure of the connector, which results from the production of a three dimensional knit forming the connecting knits, and thanks to the fact that said three dimensional knit is produced simultaneously with the first and second bidimensional knits which will form the underlay layer and the onlay layer, the liaisons between the onlay layer and the connector, and between the underlay layer and the connector, are mobile and flexible and allow a smooth twisting of each of the onlay layer, the underlay layer and the connector with respect to another, while remaining reliable.

In addition, the method of the invention allows manufacturing in one single step an integrally formed H-shaped prosthesis in which the respective properties of the underlay layer, onlay layer and connector may be tailored to meet surgical needs.

The H-shaped prosthesis of the invention may show the following features, taken alternatively or in combination:
  the underlay layer may show a pore size, measured according to the method described in Example 1 of the present application, ranging from about 1.0 mm to about 3.0 mm, preferably of about 1.1 mm×1.7 mm,
  the underlay layer may show a tensile breaking strength, measured according to the method described in Example 1 of the present application, ranging from about 100 N to about 1200 N, preferably from about 300 N to about 1000 N, preferably from about 500 to about 900 N, more preferably of about 625 N, in the warp direction, and ranging from about 100 N to about 1200 N, preferably from about 120 N to about 1000 N, preferably from about 200 N to about 500 N, more preferably of about 278 N in the weft direction,
  the underlay layer may show a bending rigidity, measured according to the method described in Example 1 of the present application, ranging from about 60 g to about 100 g, preferably of about 72 g,
  the onlay layer may show a pore size, measured according to the method described in Example 1 of the present application, ranging from about 1.7 mm×3.1 mm, preferably from about 1.5 mm to about 1.5 mm,
  the onlay layer may show a suture pull out strength, measured according to the method described in Example 1 of the present application, ranging from about 20 N to about 80 N, preferably from about 30 N to about 70 N, more preferably of about 43 N in the warp direction, and ranging from about 20 N to about 80 N, preferably from about 30 N to about 70 N, preferably of about 42 N in the weft direction, the connector may show a tensile breaking strength, measured according to the method described in Example 1 of the present application, ranging from about 30 N to 200 N, preferably from about 80 N to about 180 N, preferably from about 110 N to about 160 N, more preferably of about 139 N, in the warp direction and ranging from about 30 N to 200 N, preferably from about 80 N to about 180 N, preferably from about 110 N to about 160 N, preferably of about 143 N in the weft direction, the connector may show a tensile elongation under 50N, measured according to the method described in Example 1 of the present application, ranging from about 20% to 100%, preferably of about 36% in the warp direction and ranging from about 20% to 100%, preferably of about 54% in the weft direction, the connector may show a tensile elongation at break, measured according to the method described in Example 1 of the present application, ranging from about 60% to about 200%, preferably of about 72% in the warp direction and ranging from about 60% to about 200% preferably of about 112% in the weft direction.

The H-shaped prostheses obtained by the method of the invention may be sterilized by any means within the purview of those skilled in the art.

The H-shaped prostheses obtained by the method of the invention may be used in open surgery. They may be used for the treatment of hernia, in particular for groin hernia.

BRIEF DESCRIPTION OF THE DRAWINGS

The advantages of the method of the invention will appear more clearly from the following example and attached drawings in which.

EXAMPLE

In the present example, a base knit 1 (see FIG. 2) is formed according to the method of the invention and a H-shaped prosthesis 10 (see FIG. 6) is manufactured from the base knit 1 obtained.

The base knit 1 is produced on a spacer Raschel knitting machine comprising a first needle-bed comprising a first guide bar B1, a second guide bar B2 and a third guide bar B3, and a second needle-bed comprising a fourth guide bar B4, a fifth guide bar B5 and a sixth guide bar B6.

All guide-bars are threaded with polypropylene monofilaments having a diameter of 0.12 mm.

In the present example, the pattern unit comprises 264 courses on each needle-bed and the threading-in unit is 156. In other embodiments, the base knit could be produced with different pattern units and threading-in units.

In the present example, all the knitting patterns are given according to the ISO 11676 standard (publication year 2014).

The knitting pattern followed by bars B1, B2, B3 and B4 is the following one:

B1: (3-2-2-2/2-1-1-1/0-1-2-2)×88//
B2: (2-3-3-3/3-4-4-4/5-4-3-3)×88//
B3: (2-3-3-3/3-4-4-4/5-4-3-3)×36/(2-3-3-2/3-4-3-2/5-4-4-5)×3/(2-3-3-3/3-4-4-4/5-4-3-3)×49//
B4: (2-3-3-2/3-4-3-2/5-4-4-5)×75/1-1-1-2/1-1-1-0/1-1-1-2/4-4-6-7/6-6-6-5/6-6-6-7/6-6-6-5/(2-2-1-0/1-1-1-2/1-1-1-0/1-1-1-2/4-4-6-7/6-6-6-5/6-5-6-7/6-6-6-5)×4//
B5: (2-2-1-0/1-1-1-2/1-1-1-0/1-1-1-2/4-4-6-7/6-6-6-5/6-6-6-7/6-6-6-5)×33//
B6: (5-5-6-7/6-6-6-5/6-6-6-7/6-6-6-5/3-3-1-0/1-1-1-2/1-1-0/1-1-1-2)×33//

The threading-in of bars B1, B2, B3, B4, B5 and B6 is the following:

B1: (D.)78
B2: (S.)2(D.)31(S.)4(D.)31(S.)10
B3: (S.)2.62(S.)4.62(S.)2.16
B4: 0.140(S.)8
B5: (S.)78
B6: (S.)78 wherein a dot "." means one element empty, "D" means two yarns, "S" means a single yarn.

As a result of the above knitting pattern and threading-in unit, a base knit is obtained for which:

For needles ranging from 1 to 156, and for courses ranging from 1 to 264 on each needle-bed, a first sheet of porous knit, under the form of a bidimensional porous knit, is produced on the first needle-bed by yarns of guide-bars B1 and B2, and a second sheet of porous knit, under the form of a bidimensional porous knit, is produced on the second needle-bed by yarns guide-bars B5 and B6, For needles ranging from 67 to 74 and for courses ranging from 109 to 117, a connecting porous knit is produced, joining the first sheet of porous knit to the second sheet of porous knit, under the form of a three-dimensional porous knit, by yarns of guide-bar B3, For needles ranging from 141 to 156 and for courses ranging from 1 to 264, a pillar knit is produced, joining the first sheet of porous knit to the second sheet of porous knit, under the form of a three-dimensional knit, by yarns of guide-bar B4.

As a result, for the present example, the values of x, y, w, z, r and s of the method of the invention are the following:

x=109,
y=117,
w=67,
z=74,
r=141,
s=156.

DETAILED DESCRIPTION OF EMBODIMENTS

Figure 1:
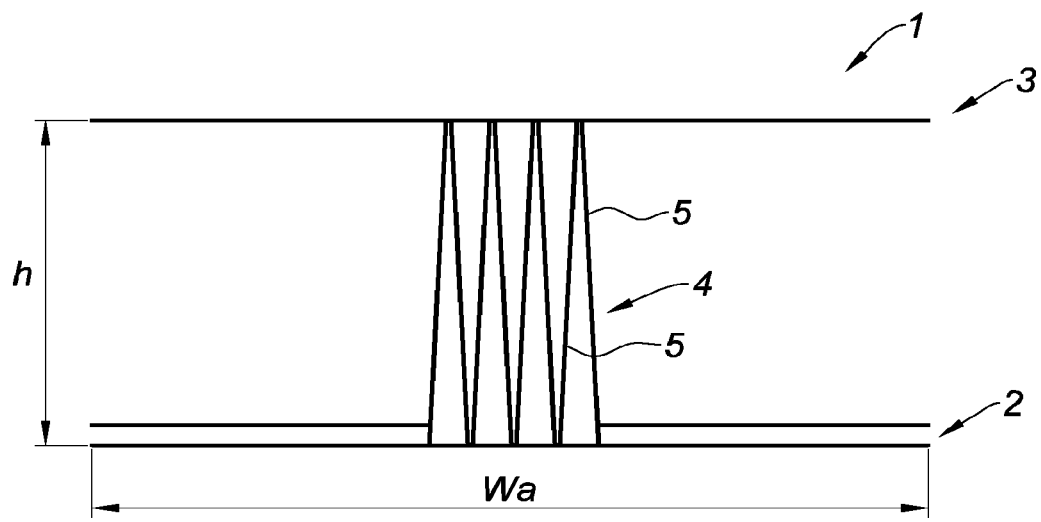
FIG. 1 is a schematic view showing the first and second sheets of porous knits and the connecting knit of a base knit obtained according to the method of the invention.

With reference to FIG. 1, where Wa indicates the warp direction, is shown schematically a part of the base knit 1 with the first sheet 2 of porous knit, the second sheet 3 of porous knit, and a connecting porous knit 4. The yarns 5 of the guide bar B3 are shown crossing from the first sheet 2, produced on the first needle-bed, to the second sheet 3, produced on the second needle-bed.

In the present example, the distance between the first needle-bed and the second needle-bed is set at about 10 mm. As a consequence, the height h of the connecting knit 4 as shown on FIG. 1 is about 10 mm.

The distance between the first needle-bed and the second needle-bed may be adjusted and designed in function of the height desired for the connecting knit, and subsequently for the connector of the H-shaped prostheses obtainable from the base knit.

The pillar knits are obtained in a similar way as the connecting porous knits but they extend on the whole production length of the base knit in the warp direction.

In the base knit 1 obtained, the first sheet 2 of porous knit and the second sheet 3 of porous knit are parallel and joined together in a discrete manner by a plurality of connecting porous knits 4 spaced apart from each other.

Figure 2:
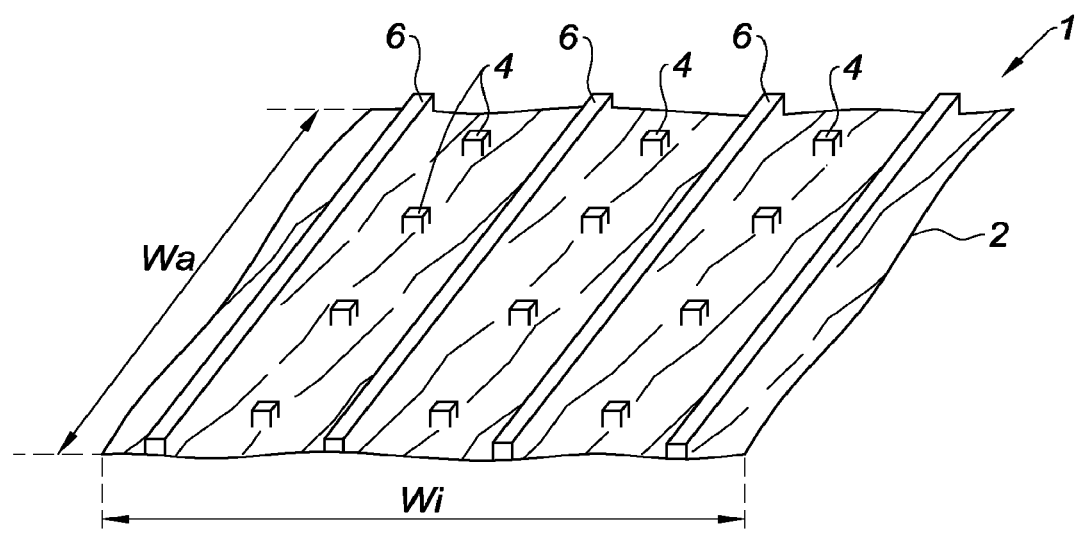
FIG. 2 is a partial perspective view of a first embodiment of a base knit obtained according to the method of the invention.

With reference to FIG. 2 is shown a part of the base knit 1 obtained with the method described herein, where the second sheet of porous knit has been removed for sake of clarity. With reference to FIG. 2 are shown the warp direction Wa and the width direction Wi of the knitting machine.

With reference to this Figure, are shown the first sheet of porous knit 2, a plurality of connecting porous knits 4 and a plurality of pillar knits 6.

A connecting knit 4 being produced for each pattern unit and each threading-in unit, the final base knit 1 comprises as many connecting knits 4 as repetitions of the pattern unit along the length of production of the base knit 1 and of the threading-in unit along the width of the machine. On the example shown, only twelve connecting knits 4 are shown. Of course, the number of connecting knits 4 in the base knit 1 may be much higher or less. For example, if the pattern unit and the threading-in unit were followed only once and were not recurring along the production length and the width of the machine (not shown on the figures), only one connecting knit 4 would be produced, thereby allowing one H-shaped prosthesis to be formed.

In the same manner, a pillar knit 6 is produced for each threading-in unit. On the example shown, only four pillar knits 6 are shown. The total number of pillar knits 6 corresponds to the total number of threading-unit that can be repeated along the width of the machine.

The pillar knits 6 run along the warp direction of the base knit 1, substantially in a continuous way. The pillar knits 6 are intended to maintain a constant distance between the first sheet 2 of porous knit and the second sheet of porous knit on the whole area of the base knit 1 when the base knit 1 is rolled up on itself on a cylinder during storage. The pillar knits 6 are intended to preserve the correct thickness of the global base knit 1, approximately 1 cm in the present example. The pillar knits 6 help avoiding that the connecting knits 4, which are intended to be used in the manufacture of the H-shaped prostheses, be shrunk by the weight of the plurality of layers of the rolled-up base knit 1.

In embodiments not shown, the pillar knits may not extend along the warp direction in a continuous way, as long as they perform the function of maintaining a constant distance between the first sheet of porous knit and the second sheet of porous knit on the whole area of the base knit when the base knit is rolled up on itself on a cylinder during storage.

Figure 3:
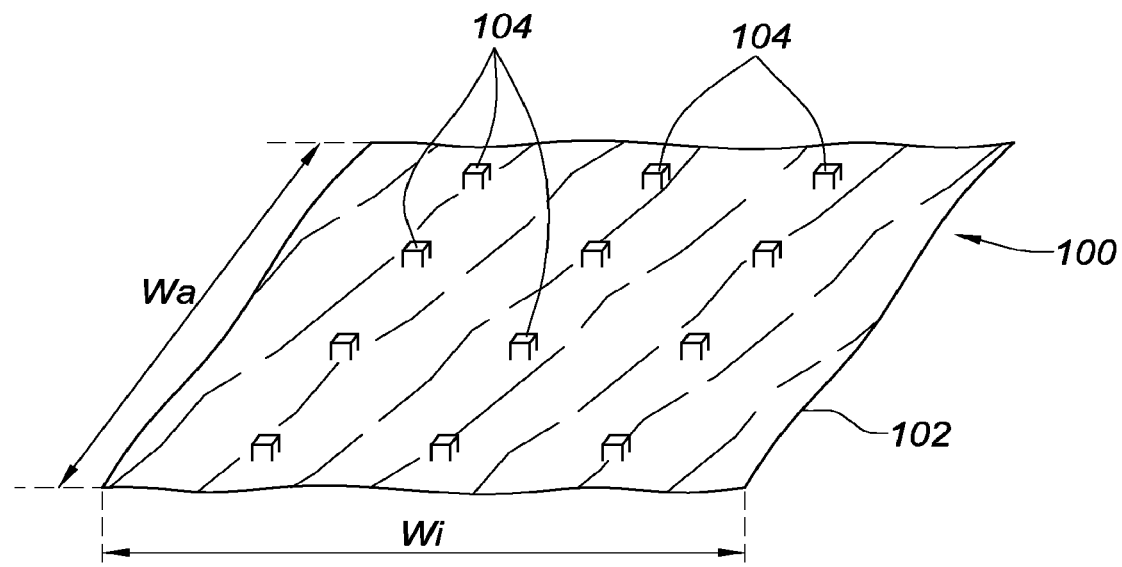
FIG. 3 is a partial perspective view of a second embodiment of a base knit obtained according to the method of the invention.

Base knits of the invention may be obtained by the method of the invention, where no pillar knits are present. With reference to FIG. 3, is shown such a base knit 100, free of any pillar knits. Such a base knit 100 may be obtained with the knitting patterns and threading-in of the present example, except for the fact that guide-bar B4 is not threaded with any yarns. The base knit 100 comprises a first sheet of porous knit 102, a second sheet of porous knit (not shown for sake of clarity) and connecting knits 104 which are identical to that of the base knit 1 of FIG. 2.

The base knit 1 is submitted to a heat-setting treatment in order to stabilize the first and second sheets (2, 3) of porous knits in the warp and weft directions and in order to stabilize the height of the connecting knits 4.

The base knit 1 is positioned in a heat-setting machine under no tension, neither in the warp direction nor in the weft direction. It is then submitted to a heat-treatment of about 140° C. The first and second sheets (2, 3) of porous knits are therefore well stabilized in the weft direction and in the warp direction and the height of the connecting knits 4 shows a shrinkage of about 50%.

Alternatively, in embodiments where the base knit is not submitted to a heat-setting treatment, the H-shaped prosthesis obtained from this base knit (see below) may be submitted to the heat-setting treatment above on its own.

Figure 4:
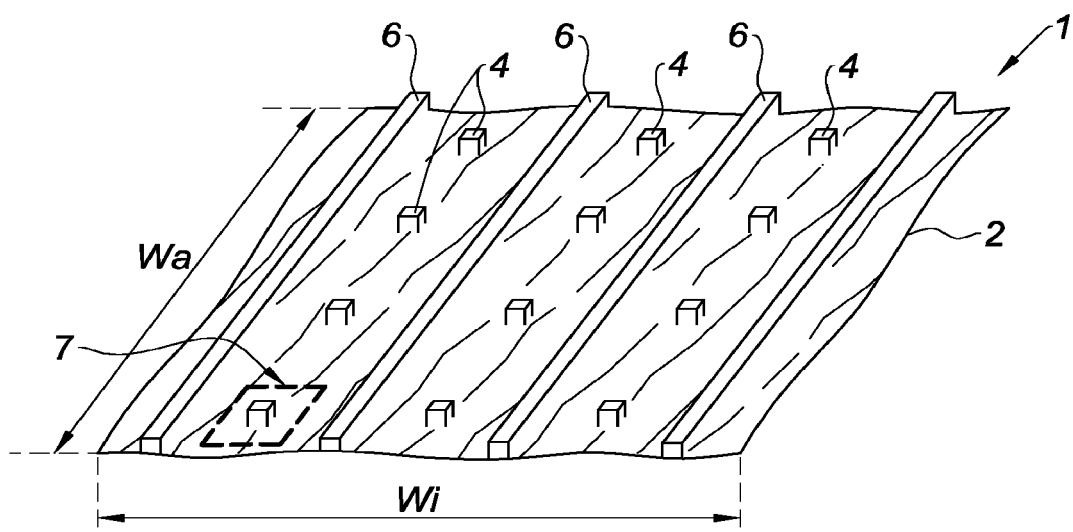
FIG. 4 is a view showing how an adequate portion of a base knit of the invention may be isolated in a view of preparing and manufacturing a H-shaped prosthesis.

With reference to FIG. 4 is shown in dotted lines an adequate portion 7 of the base knit 1 that can be selected and isolated in a view of manufacturing a H-shaped prosthesis for hernia repair. The adequate portion 7 is designed in the vicinity and around one of the connecting knits 4. The adequate portion 7 may be isolated from the base knit 1 using a pair of scissors for example. Alternatively, the adequate portion 7 may be isolated from the base knit 1 using any cutting means such as a laser, high frequency welding, etc. . . .

Figure 5:
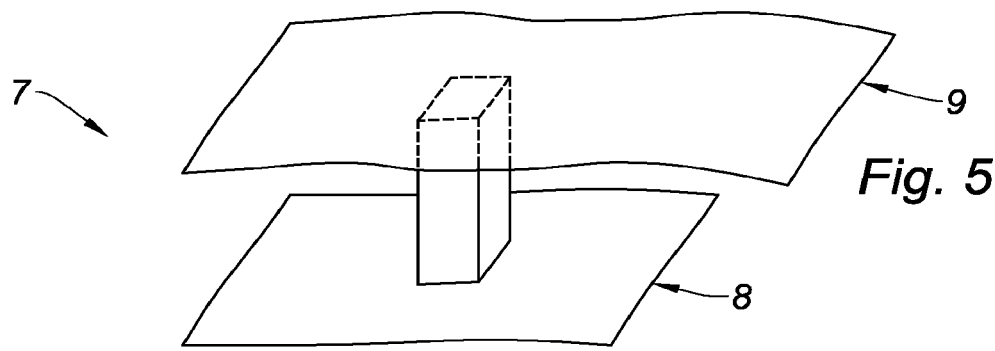
FIG. 5 is a perspective view of the adequate portion of FIG. 4 once isolated.

With reference to FIG. 5 is shown the adequate portion 7 once isolated from the base knit 1 of FIG. 4. The adequate portion 7 of the base knit comprises a portion 8 of the first sheet of porous knit, a portion 9 of the second sheet of porous knit and a connecting knit 4.

The portion 8 of the first sheet of porous knit and the portion 9 of the second sheet of porous knit are then each cut around the connecting knit 4 to the shape and dimensions desired for forming an underlay layer and an onlay layer of a H-shaped prosthesis.

Figure 6:
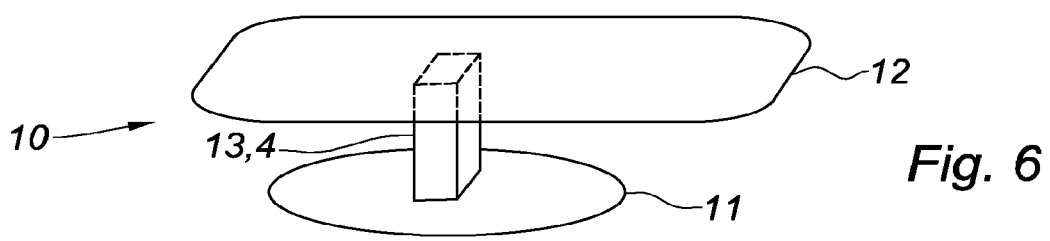
FIG. 6 is a perspective view of a H-shaped prosthesis of the invention obtained from the adequate portion of FIG. 5.
Figure 8:
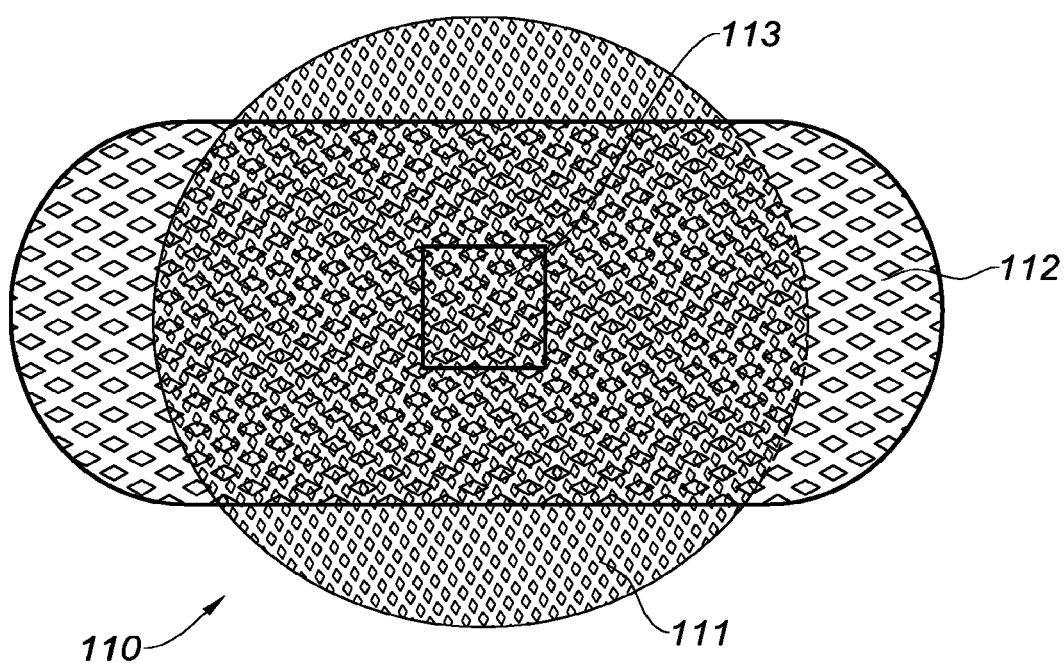
FIG. 8 is a top view of another embodiment of a H-shaped prosthesis obtained from an adequate portion as shown on FIG. 5.
Figure 9:
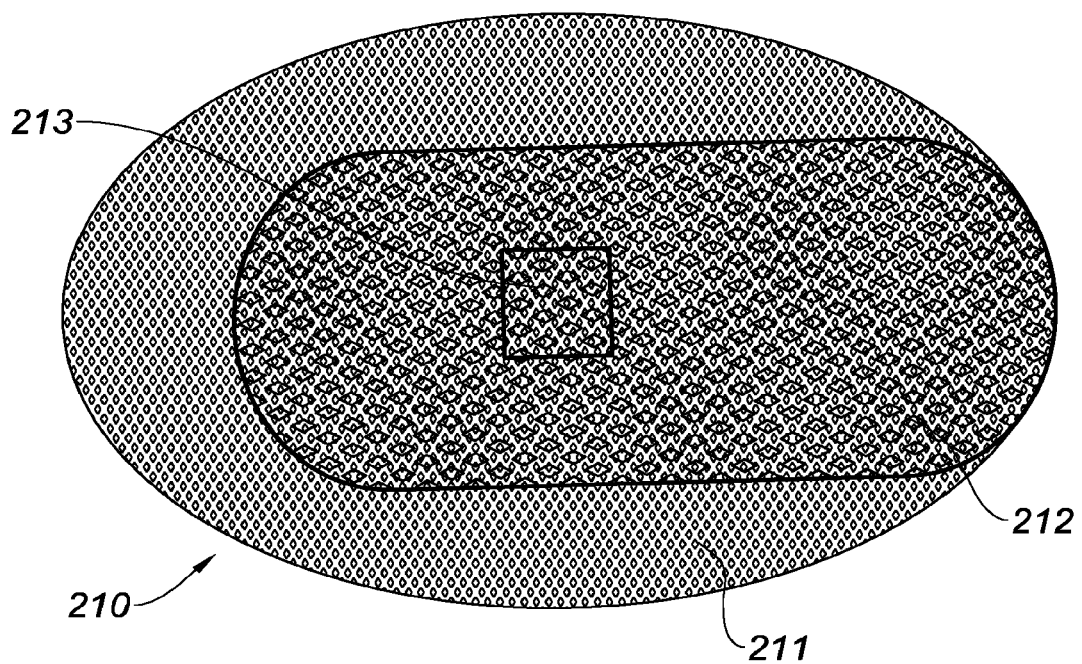
FIG. 9 is a top view of another embodiment of a H-shaped prosthesis obtained from an adequate portion as shown on FIG. 5.

With reference to FIGS. 6, 8 and 9, are shown H-shaped prostheses (10, 110, 210) thus obtained.

With reference to FIG. 6, the underlay layer 11 of the prosthesis 10 results from the cutting of the portion 8 of the first sheet of porous knit of an adequate portion 7 and has a circular shape on the example shown. The onlay layer 12 of the prosthesis 10 results from the cutting of the portion 9 of the second sheet of porous knit of an adequate portion 7 and has an oval shape on the example shown. The underlay layer 11 and the onlay layer 12 are connected together via the connector 13 (which is formed of the connecting knit 4 of the adequate portion 7). On the example shown, the connector 13 is located at the center of the underlay layer 11 but not at the center of the onlay layer 12.

With reference to FIG. 8, the underlay layer 111 of the prosthesis 110 results from the cutting of the portion 8 of the first sheet of porous knit of an adequate portion 7 and has a circular shape on the example shown. The onlay layer 112 of the prosthesis 110 results from the cutting of the portion 9 of the second sheet of porous knit of an adequate portion 7 and has an oval shape on the example shown. The underlay layer 111 and the onlay layer 112 are connected together via the connector 113, said connector 113 being, on the example shown, located at the center of the underlay layer 111 and at the center of the onlay layer 112.

With reference to FIG. 9, the underlay layer 211 of the prosthesis 210 results from the cutting of the portion 8 of the first sheet of porous knit of an adequate portion 7 and has an elliptical shape on the example shown. The onlay layer 212 of the prosthesis 210 results from the cutting of the portion 9 of the second sheet of porous knit of an adequate portion 7 and has an oval shape on the example shown. The underlay layer 211 and the onlay layer 212 are connected together via the connector 213.

As appears from FIGS. 6-9, for a H-shaped prosthesis (10, 110, 210), if the length and width of one layer, either underlay layer (11, 111, 211) or onlay layer (12, 112, 212), or of the connector (13, 113, 213), are defined as being respectively the dimension of said layer or connector in the warp direction (length) and the dimension of said layer or connector in the weft direction (width), one can see that the length and width of each layer, namely the underlay layer (11, 111, 211) and the onlay layer (12, 112, 212), in the plane of said layer, are independent of the length and width of the connector (13, 113, 213) in the plane of said layer. Similarly, the length and width of the connector (13, 113, 213) in the plane of either layer (11, 111, 211; 12, 112, 212) are independent of the length and width of said layer (11, 111, 211; 12, 112, 212) in said plane.

In other embodiments not shown, the underlay layer and the onlay layer could show different shapes, such as rectangular, square, etc. . . .

As appears clearly from the present example, since the prostheses (10, 110, 210) are produced as a single unitary structure each, there is no area of weakness at the liaisons between the underlay layer (11, 111, 211) and the connector (13, 113, 213) on one hand, and between the onlay layer (12, 112, 212) and the connector (13, 113, 213) on the other hand.

Moreover, the fact that the connector (13, 113, 213) is made from a three-dimensional porous knit allows providing a good mobility between the liaison between the underlay layer (11, 111, 211) and the connector (13, 113, 213) on one hand, and to the liaison between the connector (13, 113, 213) and the onlay layer (12, 112, 212) on the other hand.

Figure 7:
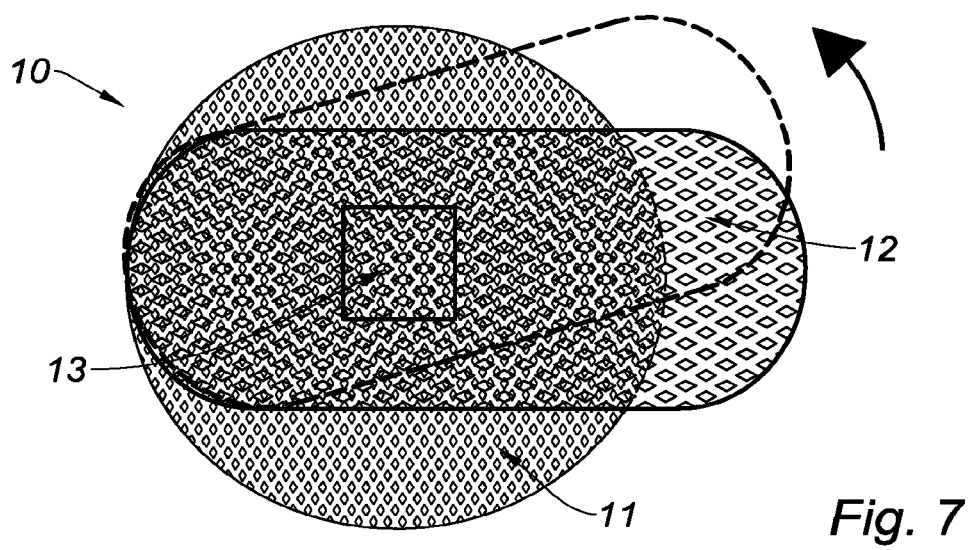
FIG. 7 is a top view of the H-shaped prosthesis of FIG. 6 showing how one layer of the prosthesis may be twisted with respect to the connector.

With reference to FIG. 7, is shown the possibility of the onlay layer 12 for example to be twisted with respect to the connector 13 for a prosthesis of the invention, for example prosthesis 10 of FIG. 6. In dotted lines is shown an angularly shifted position for the onlay layer 12, with respect to its initial position. The structure of the connector 13 obtained in the H-shaped prosthesis of the invention allows the surgeon to orientate the underlay layer and/or the onlay layer in orientations slightly different from that conferred by the initial liaisons between the connector and the underlay layer and between the connector and the onlay layer.

In addition, thanks to the structure of the connector, which results from the production of a three dimensional knit forming the connecting knits, and thanks to the fact that said three dimensional knit is produced simultaneously with the first and second bidimensional knits which then form the underlay layer and the onlay layer, the liaisons between the onlay layer and the connector, and between the underlay layer and the connector, are reliable and show good mechanical properties, such as breaking strength and elongation at break.

Such mechanical properties have been measured for the connector of the H-shaped prosthesis obtained in the present example according to the following methods:

Connector tensile breaking strength and elongation in warp and weft direction: performed on a Traction testing machine (Hounsfield model H5KS-SN 0589) with the following conditions:
5 samples
Width: 50 mm
Length: warp direction: 30 mm between the jaws
weft direction: 30 mm between the jaws
Crosshead speed: 20 mm/min
Pre-load: 0.5N
The connector is centered between the jaws.

The results as an average of the results of the five samples are collected in Table I below:

|  | Warp | Weft |
| --- | --- | --- |
| Breaking strength (N) | 139 ± 7 | 143 ± 4 |
| Elongation at 50N (%) | 36 ± 2 | 54 ± 3 |
| Elongation at break (%) | 72 ± 5 | 112 ± 11 |

Table I: tensile breaking strength and elongation of the connector

These results show that the connector of the H-shaped prosthesis obtained according to the method of the invention is particular reliable. The surgeon may twist the underlay layer or the onlay layer with respect to the connector with no fear that the unitary structure of the prosthesis be damaged.

The following mechanical properties have been measured for the underlay layer of the H-shaped prosthesis obtained in the present example according to the following methods:
Pore size: measured according to NF S94-801: 2007 "Reinforcing implants positioned via the vaginal route to treat effort urinary incontinence and/or pelvic organs prolapsus—Pre-Clinital tests and clinical tests"—§ 5.3.3 method b, with a profile projector ORAMA
Tensile breaking strength (N), tensile elongation (%) and elongation under 50 N (%): are measured according to ISO 13934-1: 1999 *"Determination of breaking strength and elongation"*, 5 samples, width: 50 mm, length in the warp direction: 200 mm between the jaws, length in the weft direction: 120 mm between the jaws, Crosshead speed: 100 mm/min, Pre-load: 0.5 N, using a traction testing machine such as the Hounsfield model H5KS (Hounsfield, Redhill, England),
Bending rigidity in warp and weft direction: 5 samples of dimensions 50×100 mm, with a slot space of 15 mm on a Handle-O-Meter machine
The results are as follows:
Pore size (width mm×height mm): 1.1 mm×1.7 mm,
Tensile breaking strength: 625 N in the warp direction and 278 N in the weft direction,
Bending rigidity: 72 g The underlay layer of the prosthesis of the present example therefore shows adequate pore size and mechanical properties so that it can deploy easily in the abdominal cavity and perform efficiently its wall reinforcing function.

The following mechanical properties have been measured for the onlay layer of the H-shaped prosthesis obtained in the present example according to the following methods:

Pore size: same method as for the underlay above,

Suture pull out strength in the warp direction and in the weft direction: measured according to NF S94-801: 2007 "Reinforcing implants positioned via the vaginal route to treat effort urinary incontinence and/or pelvic organs prolapsus—Pre-Clinical tests and clinical tests"—§ 5.2.3: a USP 2 suture yarn is passed through a pore of a 50×100 mm sample, and is tracted away using a traction testing machine such as the Hounsfield model H5KS (Hounsfield, Redhill, England) with the following conditions: 5 samples, width 50 mm, 100 mm between the jaws, crosshead speed: 100 mm/min.

The results are as follows:

Pore size: 1.7 mm×3.1 mm

Suture pull out strength: 43 N in the warp direction and 42 N in the weft direction.

The onlay layer of the prosthesis of the present example therefore shows adequate pore size and mechanical properties so that it shows a good flexibility, visibility and a good conformability, while being suturable. Moreover, the softness and conformability of the onlay layer helps positioning the prosthesis with regards to the abdominal wall.

The knitting method of the present example allows producing a base knit from which a plurality of H-shaped prosthesis may be obtained, in one single step, rapidly and efficiently. Since the base knit is obtained as a unitary knitted structure, there is no area of weakness between the first bidimensional porous knit and the connecting knit on one hand, and between the second bidimensional porous knit and the connecting knit on the other hand. In addition, the knitting method of the invention allows using different knitting patterns for the onlay layer and for the underlay layer: the performance characteristic of each layer can therefore be tailored to meet the clinical needs and surgeon preference, in a single manufacturing process without the need for additional manufacturing/assembly steps.

Moreover, each H-shaped prosthesis obtained from the base knit of the present example is itself obtained as a unitary structure. There is therefore no area of weakness at the liaisons between the underlay layer and the connector on one hand, and between the onlay layer and the connector on the other hand.

In addition, for each H-shaped prosthesis cut from the base knit produced according to the method of the invention, the liaisons between the underlay layer and the connector on one hand, and between the onlay layer and the connector on the other hand show a mobility and a flexibility allowing a surgeon to orientate freely the underlay layer and/or the onlay layer in directions that may differ from the initial orientations of such layers with respect to the connector, without jeopardising the efficiency and the integrity of the H-shaped prosthesis.

What is claimed is:

1. An H-shaped prosthesis suitable for hernia repair, said H-shaped prosthesis comprising an underlay layer, an onlay layer, and a connector, said underlay layer, onlay layer and connector being formed as an unitary knitted structure, wherein a length and width of each of the underlay layer and the onlay layer are independent of a length and width of said connector in a plane of said layer, the length and width of the connector in the plane of one layer being independent of the length and width of said layer in said plane.

2. The prosthesis according to claim 1, wherein the connector includes a tensile breaking strength ranges from about 80 N to about 180 N in a warp direction.

3. The prosthesis according to claim 1, wherein the connector includes a tensile breaking strength ranges from about 110 N to about 160 N in a warp direction.

4. The prosthesis according to claim 1, wherein the connector includes a tensile breaking strength ranges from about 80 N to about 180 N in a weft direction.

5. The prosthesis according to claim 1, wherein the connector includes a tensile breaking strength ranges from about 110 N to about 160 N in a weft direction.

6. The prosthesis according to claim 1, wherein the connector includes a tensile elongation under 50N ranging from about 20% to about 100% in a warp direction and ranging from about 20% to about 100% in a weft direction.

7. The prosthesis according to claim 1, wherein the connector includes a tensile elongation at break ranging from about 60% to about 200% in a warp direction and ranging from about 60% to about 200% in a weft direction.

8. The prosthesis according to claim 1, wherein the connector includes a tensile elongation at break of about 72% in a warp direction and about 112% in a weft direction.

9. The prosthesis according to claim 1, wherein the underlay layer and the onlay layer are each a bidimensional porous knit and the connector is a three-dimensional porous knit.

10. The prosthesis according to claim 1, wherein the underlay layer and the onlay layer are connected together via the connector being located at a center of the underlay layer and a center of the onlay layer.

11. The prosthesis according to claim 1, wherein the underlay layer and the onlay layer define the same shape.

12. The prosthesis according to claim 1, wherein the underlay layer and the onlay layer define different shapes.

13. The prosthesis according to claim 1, wherein the underlay layer and the onlay layer are parallel to each other.

14. The prosthesis according to claim 1, wherein the connector is perpendicular to the underlay layer and the onlay layer.

15. The prosthesis according to claim 1, wherein said unitary knitted structure includes one or more biocompatible yarns.

16. The prosthesis according to claim 15, wherein the one or more biocompatible yarns are monofilaments.

17. The prosthesis according to claim 16, wherein the monofilaments have a diameter ranging from about 0.07 mm to about 0.30 mm.

18. The prosthesis according to claim 15, wherein the one or more biocompatible yarns are made of polypropylene.

19. The prosthesis according to claim 1, wherein said prosthesis is heat set.

20. An H-shaped prosthesis suitable for hernia repair, said H-shaped prosthesis comprising an underlay layer, an onlay layer, and a connector, said underlay layer, onlay layer and connector being formed as an unitary knitted structure, wherein the underlay layer, the onlay layer, or both are configured to be twisted in a direction that may differ from an initial orientation.

21. The H-shaped prosthesis of claim 20, wherein the underlay layer, the onlay layer, or both are configured to be twisted in a direction that may differ from an initial orientation with respect to the connector without damaging the unitary knitted structure.

* * * * *